United States Patent [19]

Seto

[11] Patent Number: 5,731,207
[45] Date of Patent: Mar. 24, 1998

[54] TRANSFERRING METHOD AND DEVICE FOR DRY CHEMICAL ANALYSIS FILM

[75] Inventor: Yoshihiro Seto, Kanagawa-ken, Japan

[73] Assignee: Fuji Photo Film Co., Ltd., Kanagawa, Japan

[21] Appl. No.: 698,162

[22] Filed: Aug. 7, 1996

[30] Foreign Application Priority Data

Aug. 8, 1995 [JP] Japan .................................. 7-202403

[51] Int. Cl.$^6$ .................................................. G01N 35/10
[52] U.S. Cl. ........................ 436/46; 436/44; 436/50; 436/807; 422/63; 422/64; 422/66; 422/67; 422/104
[58] Field of Search ........................ 436/43, 44, 46, 436/48, 50, 54, 183, 807; 422/63, 64, 66, 67, 103, 104

[56] References Cited

U.S. PATENT DOCUMENTS 4,807,984  2/1989  Kurimura et al. ....................... 350/529
4,994,240  2/1991  Hayashi ................................. 422/63

FOREIGN PATENT DOCUMENTS 0064691  11/1982  European Pat. Off. .
0567067  10/1993  European Pat. Off. .

*Primary Examiner*—Long V. Le
*Attorney, Agent, or Firm*—Sughrue, Mion, Zinn, Macpeak & Seas, PLLC

[57] ABSTRACT

A frameless chemical analysis film includes a reagent layer formed on a support sheet. When the frameless chemical analysis film which has been held on a resilient suction pad under a suction force supplied to the suction pad is transferred to a predetermined member, the suction force supplied to the suction pad is gradually released taking at least a time which the suction pad, which has been deformed under the suction force, takes to be restored to the original shape.

8 Claims, 4 Drawing Sheets

TRANSFERRING METHOD AND DEVICE FOR DRY CHEMICAL ANALYSIS FILM

BACKGROUND OF THE INVENTION

1. Field of the Invention

This invention relates to a method of and a device for transferring a dry frameless chemical analysis film in a biochemical analysis system or the like in which a sample liquid such as blood or urine is spotted onto a frameless chemical analysis film carrying thereon a reagent layer whose optical density changes through a chemical reaction, a biochemical reaction, an immunoreaction or the like with a specific biochemical component contained in the sample liquid and the concentration, activity or the like of the specific biochemical component contained in the sample liquid is quantitatively analyzed through the change in optical density.

2. Description of the Related Art

There has been put into practice a "dry-to-the-touch" chemical analysis slide with which the concentration of a specific chemical component contained in a sample liquid, the activity thereof or the content of a solid component can be quantitatively analyzed by only spotting a droplet of the sample liquid on the film. When quantitatively analyzing the chemical components or the like contained in a sample liquid using such a dry chemical analysis slide, a droplet of the sample liquid is spotted on the slide and is held at a constant temperature for a predetermined time (incubation) in an incubator so that coloring reaction occurs, and the optical density of the color formed by the coloring reaction is optically measured. That is, measuring light containing a wavelength which is pre-selected according to the combination of the component to be analyzed and the reagent contained in the reagent layer of the slide is projected onto the slide and the optical density of the slide is measured. Then the concentration or the activity of the component to be analyzed is determined on the basis of the optical density using a calibration curve which represents the relation between the concentration of the biochemical component and the optical density.

The chemical analysis slide comprises a chemical analysis film in the form of a chip and a frame of organic polymer or the like which supports flat the film chip. As such a dry chemical analysis film, there has been known an integrated multi-layered chemical analysis film comprising a support of organic polymer or the like and a reagent layer formed on the sheet. A spreading layer is sometimes formed over the reagent layer. Further there has been known a dry chemical analysis film which is formed of filter paper and has one or more layers.

In a chemical analysis system we have proposed previously, the film chip is used as it is without frame (will be referred to as "frameless chemical analysis film", hereinbelow) as disclosed, for instance, in U.S. patent Ser. No. 08/591,904.

In the system, the frameless chemical analysis film is taken out from a supplier and transferred to the incubator by use of a transferring suction pad.

However the system involves the following problem. That is, when the system is arranged so that the frameless chemical analysis film is inserted into the incubator as it is held on the transferring suction pad, the incubator must be provided with an open passage through which the transferring suction pad is moved into the incubator, which makes it difficult to incubate the frameless chemical analysis film in an air-tight fashion. When the space around the film is not isolated from the exterior in an air-tight fashion, the measuring accuracy deteriorates due evaporation of the sample liquid and/or contamination by other gasses.

Accordingly it is necessary for the transferring pad to release the frameless chemical analysis film to transfer it to another transferring means or to the incubator. In such transfer of the film, there has been a problem that the film jumps off the transferring pad or to a position where the film cannot be located in place on said another transferring means or the incubator, which can give rise to trouble in subsequent processing.

Such jumping of the frameless chemical analysis film is caused by resiliency of the suction pad when the suction pad, which has been deformed by a suction force supplied thereto while holding the frameless chemical analysis film, is restored to the original shape in response to release of the suction force. Normally such a phenomenon hardly occurs since the frameless chemical analysis film is generally attracted against the suction pad under an electrostatic force or the like. However, for instance, when a foreign matter is between the suction pad and the film, such a phenomenon can occur.

SUMMARY OF THE INVENTION

In view of the foregoing observations and description, the primary object of the present invention is to provide a method of and a device for transferring a frameless chemical analysis film which can prevent the film from jumping upon release of the suction force to the suction pad, whereby the film can be surely transferred.

In accordance with the present invention, when the frameless chemical analysis film which has been held on a resilient suction pad under a suction force supplied to the suction pad is transferred to a predetermined member, the suction force supplied to the suction pad is gradually released taking at least a time which the suction pad, which has been deformed under the suction force, takes to be restored to the original shape. The time required to release the suction force can be elongated by increasing the resistance of a passage for opening the suction pad to atmosphere, for instance, by elongating the passage or providing an orifice in the passage, or slowly opening an air valve.

The transferring device in accordance with the present invention comprises a transferring means provided with a resilient suction cup which holds the frameless chemical analysis film under a suction force supplied thereto through a vacuum line, an air passage which opens the vacuum line to atmosphere and an air flow control means which, when the suction pad is to release the frameless chemical analysis film, controls the flow rate of air in the air passage to gradually introduce air into the vacuum line so that the pressure in the vacuum line increases to a release pressure, at which the suction pad releases the frameless chemical analysis film, taking at least a time which the suction pad, which has been deformed under the suction force, takes to be restored to the original shape.

With this arrangement, the suction pad is gradually restored and accordingly resiliency of the suction pad does not act rapidly, whereby the frameless chemical analysis film can be stable in a predetermined position on the suction pad without jumping even after the suction force is released and can be accurately located with respect to the member which receives the frameless chemical analysis film.

Accordingly the frameless chemical analysis film can be surely transferred and reliability of the biochemical analysis system can be improved. Further by use of a frameless chemical analysis film, systems using chemical analysis elements may be smaller in size as compared with when the aforesaid chemical analysis slides are used. Further the frameless chemical analysis film can be manufactured at cost lower than the chemical analysis slide with frame.

DESCRIPTION OF THE PREFERRED EMBODIMENT

Figure 1:
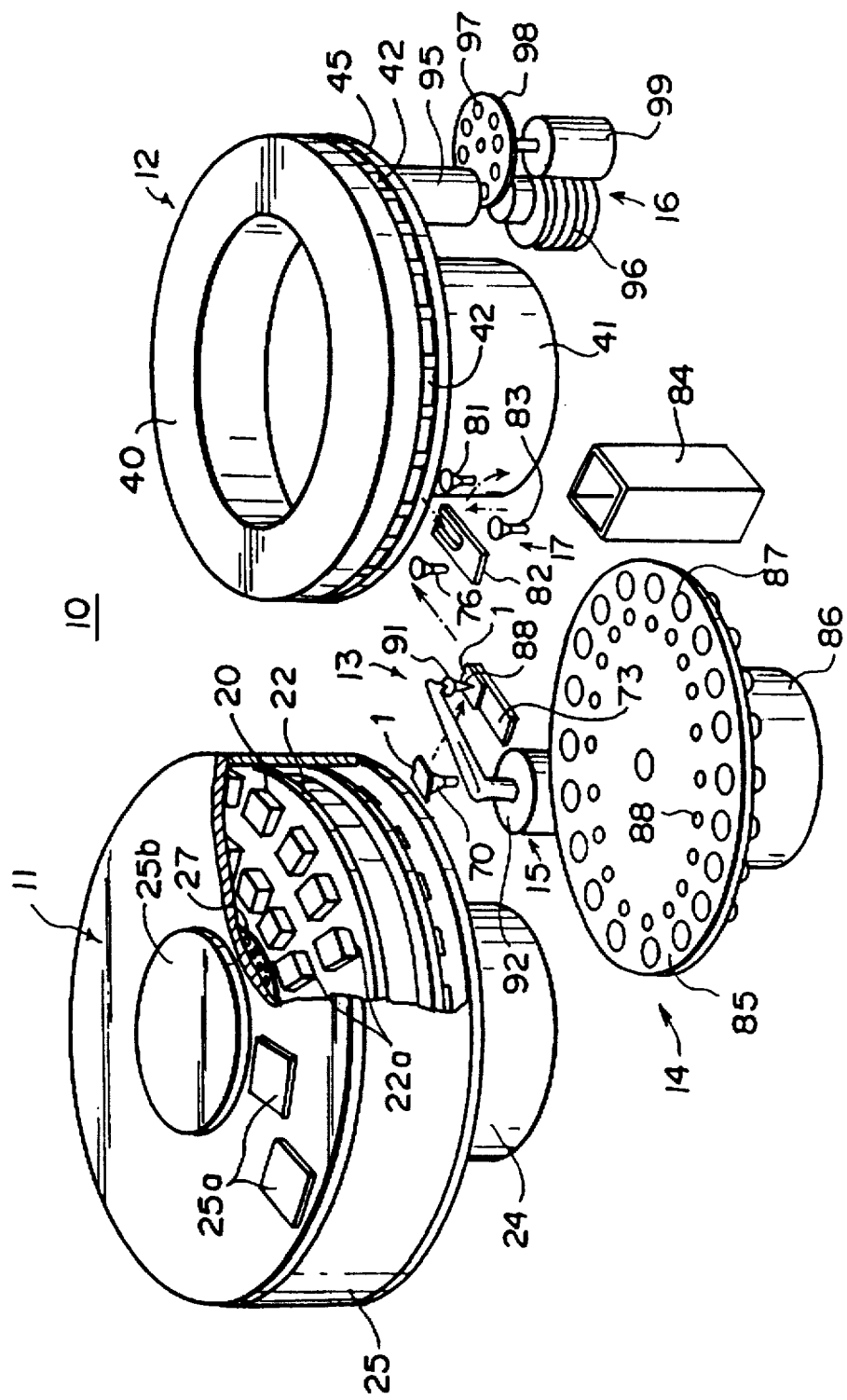
FIG. 1 is a schematic perspective view showing a biochemical analysis apparatus provided with a frameless chemical analysis film transferring device in accordance with an embodiment of the present invention.

In FIG. 1, a biochemical analysis apparatus 10 provided comprises a film supplier 11 in which a plurality of virgin dry frameless chemical analysis films 1 (which are rectangular or square in shape) are stored, an incubator 12 which is disposed beside the film supplier 11 and incubates the frameless chemical analysis films 1 spotted with sample liquids for a predetermined time at a constant temperature, a film transfer means 13 which transfers the frameless chemical analysis films 1 from the film supplier 11 to the incubator 12, a sample liquid supplier 14 in which a plurality of sample liquids such as serum, urine or the like are stored, a spotting mechanism 15 which spots one of the sample liquids in the sample liquid supplier 14 on the frameless chemical analysis film 1 on the way to the incubator 12, and a light measuring system 16 disposed below the incubator 12.

Figure 2:
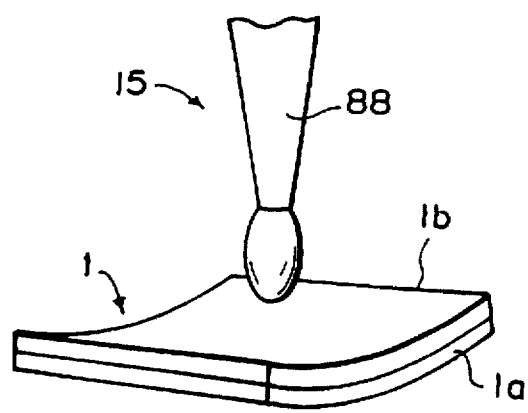
FIG. 2 is a perspective view showing spotting of the sample liquid onto the frameless chemical analysis film.

As shown in FIG. 2, the frameless chemical analysis film 1 comprises a light-transmissive support sheet 1a formed of plastic film such as polyethylene terephthalate (PET), polystyrene or the like, a reagent layer 1b including a spreading layer. If desired a protective layer (not shown) formed of a material resistant to rubbing such as fabric may be formed over the reagent layer, and such a protective layer may double as the spreading layer.

In a dry state, the film 1 is warped (curled or curved) toward the reagent layer 1b, the degree of warp depending upon the kind of the reagent layer 1b and the dryness of the film 1. The reagent layer 1b of the frameless chemical analysis film 1 contains therein reagent (chemical analysis reagent or immunoassay reagent) which makes a coloring reaction (coloring substance forming reaction) with a particular component in the sample liquid spotted from a nozzle tip 88 of a spotting means 15 (to be described later) after incubation for a predetermined time. A plurality of kinds of frameless chemical analysis films 1 having reagent layers 1b for different analytes (chemical component or solid component to be analyzed) are prepared.

Figure 3:
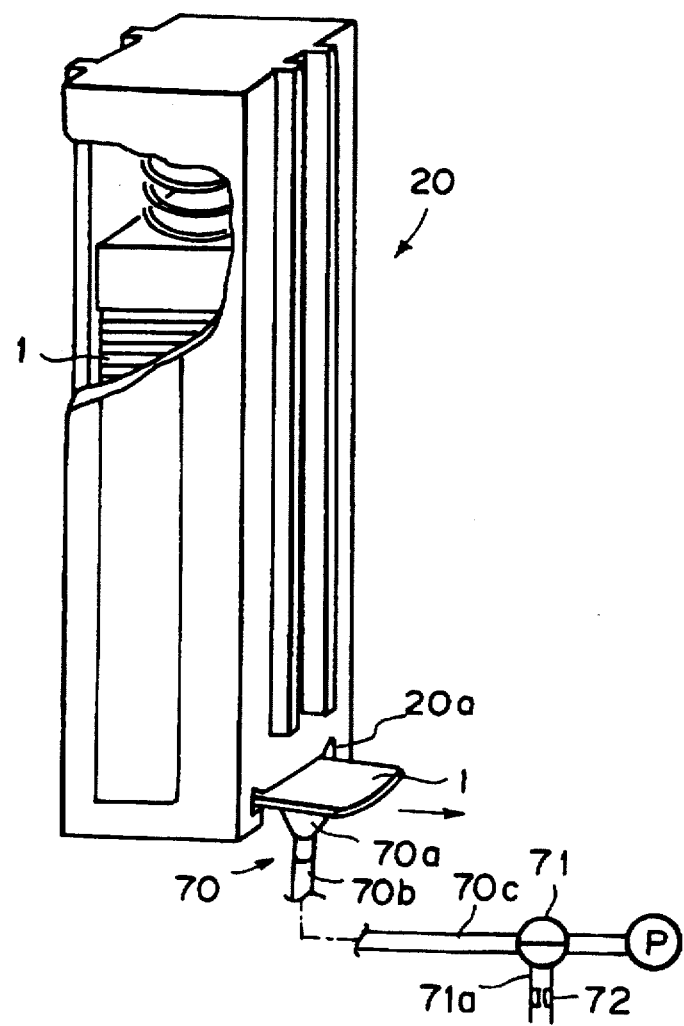
FIG. 3 is a perspective view showing the manner of taking out the frameless chemical analysis film from the cartridge.

The chemical analysis films 1 are stacked in cartridges 20 shown in FIG. 3 for the respective analytes with the support sheets 1a facing downward. A plurality of the cartridges 20 are respectively loaded in a plurality of cartridge holding portions 22a formed in a disk-like support member 22 in the film supplier 11 in inner and outer circles. The support member 22 is supported for rotation on a base 24 and is rotated by a supplier motor (not shown) to bring a desired cartridge 20 to a film takeout position where the film transfer means 13 takes out the film 1 in the cartridge 20.

The film supplier 11 is provided with a cover 25 which tightly encloses the inner space of the film supplier 11. The cover 25 is provided with a pair of openings 25a provided with lids and the cartridges 20 are taken out and inserted into the cartridge holding portions through the openings 25a. An dehumidifying agent holding portion 27 is formed in the support member 22 at the center thereof and dehumidifying agent (desiccant) is loaded in the dehumidifying agent holding portion through an opening 25b formed in the cover 25. The opening 25b is provided with a lid. Thus the inner space of the film supplier 11 is kept dry.

A shutter (not shown) is provided in the lower surface of the film supplier 11 in the film takeout position. The shutter is opened when the film 1 is taken out from the cartridge 20 and a film take-out member 70 of the film transfer means 13 takes out the lowermost film 1 in the cartridge 20 through the shutter.

Each of the cartridges 20 are loaded so that a film take-out port 20a (FIG. 3) is directed toward the center of the support member 22. The film take-out port 20a extends in a radial direction of the support member 22 in the bottom wall of the cartridge 20. The film take-out member 70 has a suction pad 70a and the suction pad 70a is inserted into the cartridge 20 through the film take-out port 20a in the bottom wall of the cartridge 20 and attracts the lowermost film 1 under a suction force. Then the suction pad 70a is moved toward the center of the support member 22 to take out the film 1.

The incubator 12 shown in FIG. 1 comprises a disk-like body portion 40 which is supported to be rotated by a drive mechanism 41 disposed below the body portion 40 at the center thereof. A plurality of cells 42 are provided in the body portion 40 at predetermined intervals in the circumferential direction thereof. The chemical analysis films 1 are incubated in the cells 42.

Figure 4:
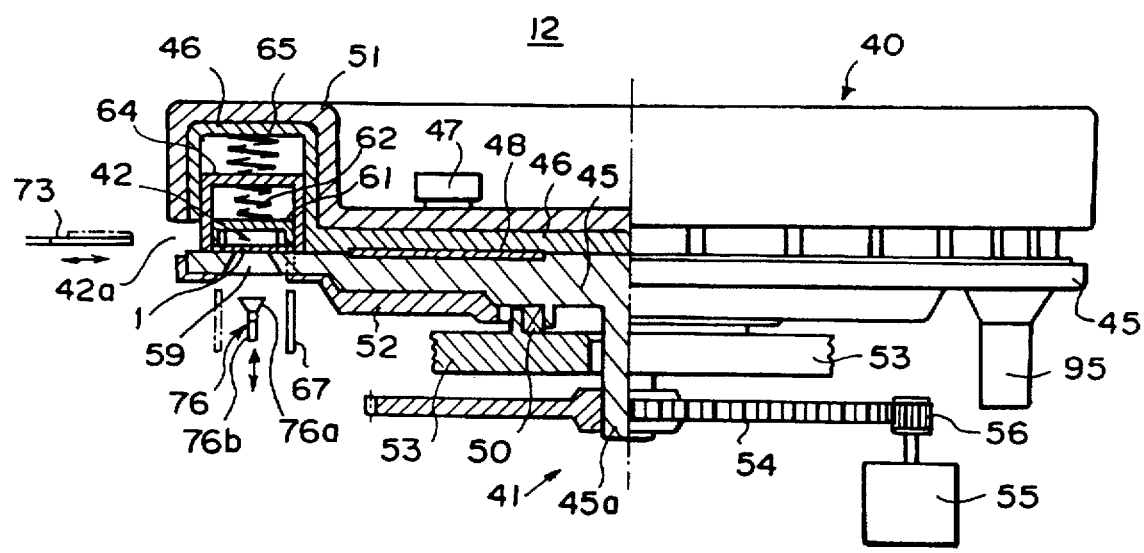
FIG. 4 is a front view partly in cross-section of the incubator.

As shown in FIG. 4, the body portion 40 comprises a lower disk 45 of metal having a flat upper surface and an upper disk 46 of metal connected to the lower disk 45 by a screw 47. The peripheral edge portion of the upper disk 46 is bulged upward to form an annular channel open downward. The lower edge of the outer peripheral edge of the upper disk 46 is spaced from the upper surface of the lower disk 45 to form a space which opens in the side surface of the incubator 12 and gives access to the cells 42. A heater 48 is disposed in the body portion 40 between the lower and upper disks 45 and 46 and the chemical analysis films 1 in the cells 42 are heated to a predetermined temperature (e.g., 37° C.) and held at the temperature. The disks 45 and 46 are formed of a material such as aluminum having a high heat conductivity. The outer surfaces of the upper and lower disks 46 and 45 are covered with heat insulating materials 51 and 52.

The body portion 40 is supported for rotation about a rotary shaft 45a relative to a base 53 by way of a bearing 50 on the lower surface of the lower disk 45. A gear 54 is fixed to the rotary shaft 45a and in mesh with a drive gear 56 of a disk drive motor 55. Thus the body portion 40 is rotated by the disk drive motor 55.

A plurality of light measuring windows 59 for photometry are formed in the lower disk 45 at predetermined intervals to be opposed to the respective cells 42. A film pressing member 61 for fixing the chemical analysis film 1 in a predetermined position in the cell 42 and a cell cover 64 which encloses the film 1 in an air-tight fashion are provided in each of the cells 42. A measuring system 16 has a light measuring head 95 which is disposed below the body portion 40 in a light measuring position.

Figure 5:
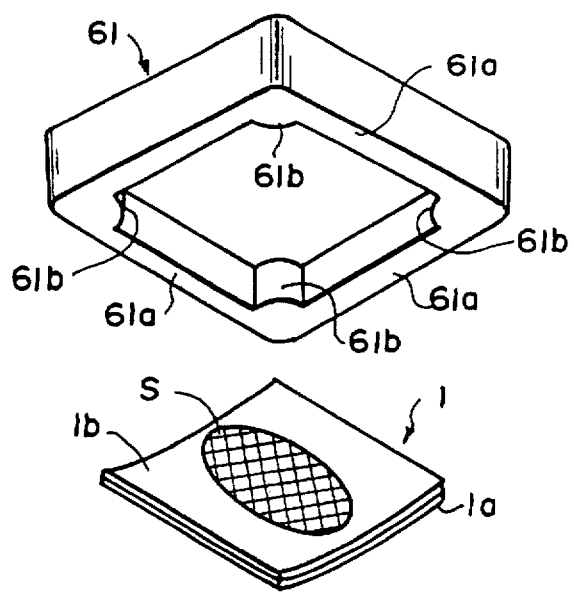
FIG. 5 is a perspective view showing the film pressing member and the frameless chemical analysis film spotted with the sample liquid.

As shown in FIG. 5, the film pressing member 61 has a square frame portion 61a on the lower surface thereof. The inner dimensions of the frame portion 61a is larger than the outer dimensions of the frameless chemical analysis film 1 and a protrusion 61b is provided at each corner of the frame portion 61a to project inward. When the film pressing member 61 is moved downward against the film 1, only the protrusions 61b are brought into contact with the film 1 so that the pressing member 61 is not brought into contact with the portion S over which the sample liquid can spread. The film pressing member 61 is urged downward under the force of a spring 62 provided on the upper surface of the film pressing member 61.

The cell cover 64 is in the form of a square box open downward and is fitted in the upper disk 46 to be movable up and down. The spring pressing member 61 is received in the cell cover 64 and the cell cover 64 is urged downward by a spring 65 provided on the upper surface thereof. When the lower surface of the cell cover 64 is pressed against the upper surface of the lower disk 45, the frameless chemical analysis film 1 is enclosed therein in an air-tight fashion. The film pressing member 61 is slidably received in the cell cover 64 with the spring 62 compressed between the upper surface of the film pressing member 61 and the upper wall of the cell cover 64. The film pressing member 61 is moved upward together with the cell cover 64.

A push rod 67 is inserted into the cell 42 through the lower disk 45 to lift the cell cover 64 overcoming the force of the spring 65. Such a push rod 67 is disposed in each of a film insertion position and a film discharge position and lifts the cell cover 64 together with the film pressing member 61 when the frameless chemical analysis film 1 is inserted into the cell 42 or discharged from the cell 42.

The film transfer means 13 for transferring the film 1 from the film supplier 11 to the incubator 12 comprises said film take-out member 70 with said suction pad 70a for taking out the film 1 from the cartridge 20, a horseshoe-like delivery member 73 which receives the film 1 held on the suction pad 70a from below the film 1 with the spreading layer 4 facing upward and inserts the film 1 into the cell 42 in the incubator 12, and a suction member 76 which moves in and out the cell 42 from below the cell 42 and receives the film 1 held by the delivery member 73 inside the cell 42.

As shown in FIG. 3, the film take-out member 70 has the suction pad 70a which is directed upward and holds the lower surface of the support sheet 1a of the frameless chemical analysis film 1 under a suction force. The suction pad 70a is supported by a conveying base portion 70b and a suction hose 70c connects the suction pad 70a to a suction pump P by way of an air valve 71. The conveying base portion 70b is moved back and forth and up and down by a drive mechanism (not shown) to move the suction pad 70a back and forth and up and down.

The suction pad 70a is formed of a resilient material. The air valve 71 is controlled by a control circuit (not shown) and selectively connects the suction pad 70a to the suction pump P and to an air passage 71a which opens the suction hose 70c to atmosphere. That is, when the suction pad 70a is to attract the frameless chemical analysis film 1, the air valve 71 connects the suction pad 70a to the suction pump P and when the suction pad 70a is to release the frameless chemical analysis film 1 to deliver it to the delivery member 73, the air valve 71 connects the suction pad 70a to the air passage 71a. An orifice 72 is provided in the air passage 71a to control the flow rate of air in the air passage 71a to gradually introduce air into the suction pad 70a so that the pressure in the suction pad 70a increases to a release pressure, at which the suction pad 70a releases the frameless chemical analysis film 1, taking at least a time which the suction pad 70a, which has been deformed under the suction force, takes to be restored to the original shape.

The orifice 72 is to elongate the time required to release the suction force by reducing the effective cross-sectional area of the air passage 71a to increase the resistance of the air passage 71a. The time required to release the suction force may also be elongated by use of a long air passage 71a, or slowly opening the air valve 71.

The suction pad 70a is moved upward and into the cartridge 20 through the opening in the bottom of the cartridge 20 and holds the support sheet 1a of the lowermost frameless chemical analysis film 1 under the suction force. Then the suction pad 70a is slightly moved downward holding the film 1 and then moved horizontally toward the center of the support member 22 to take out the film 1 through the film take-out portion 20a in the side wall of the cartridge 20. Thereafter the suction pad 70a is moved downward outside the film supplier 11 through the opening in the cover 25 and moved away from the center of the support member 22 to convey the film 1 to a spotting position.

Figure 6:
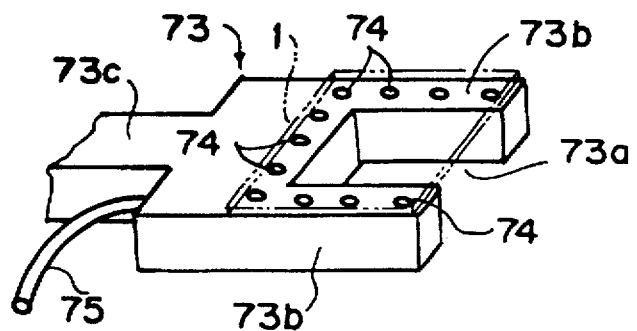
FIG. 6 is a fragmentary perspective view of the film delivery member.

As shown in FIG. 6, the delivery member 73 is like a horseshoe in shape and has a flat upper surface. That is, the delivery member 73 is bifurcated in the front end portion to form of a pair of arm portions 73b extending on opposite sides of a cutaway portion 73a, and a plurality of suction holes 74 are formed to surround the cutaway portion 73a and to open in the upper surface of the delivery member 73. The suction holes 74 are connected to a suction pump (not shown) through vacuum tube 75. The base portion 73c of the delivery member 73 is connected to a drive mechanism (not shown) to be moved from the spotting position toward the center of the incubator 12 and inserted into the cell 42 through the side opening 42a of the incubator 12.

Figure 7A:
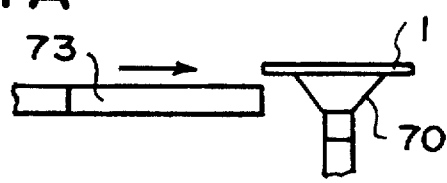
FIGS. 7A to 7C are views for illustrating transfer of the frameless chemical analysis film from the suction pad to the film delivery member.
Figure 7B:
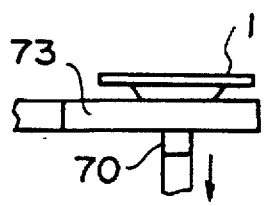
Figure 7C:
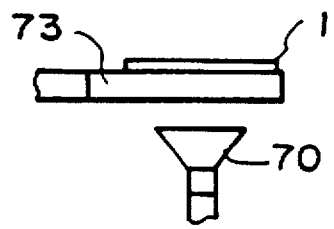

When the delivery member 73 receives the frameless chemical analysis film 1 from the suction pad 70a, the delivery member 73 is moved toward the suction pad 70a holding the film 1 as shown in FIG. 7A, and is stopped in a position where the suction pad 70a is in the cutaway portion 73a of the delivery member 73 with the film 1 positioned above the cutaway portion 73a as shown in FIG. 7B. Then the suction pad 70a is moved downward below the delivery member 73 leaving the film 1 on the delivery member 73. The film 1 left on the delivery member 73 is held thereon under the suction force provided through the suction holes 74. Between the state shown in FIGS. 7B and 7C, the suction force applied to the suction pad 70a is released before the frameless chemical analysis film 1 is brought into contact with the delivery member 73. At this time since the suction force is released taking a long time by virtue of the orifice 72 as described above, the film 1 cannot be flicked away from the suction pad 70a under the resiliency of the pad 70a. Thus the film 1 is can be held in place relative to the suction pad 70a and accordingly the film 1 can be transferred to the delivery member 73 accurately in place, whereby a predetermined amount of the sample liquid can be accurately spotted by the spotting means 15 onto the center of the reagent layer 1b held by the delivery member 73.

Said suction member 76 positioned below the cell 42 in the incubator 12 has a suction pad 76a directed upward and is moved up and down by a drive mechanism (not shown) into and away from the cell 42 through the light measuring window 59 in the bottom of the cell 42. The suction pad 76a is connected to a suction pump (not shown) through a vacuum tube. The suction pad 76a may also be provided with the mechanism for elongating the time required to release the suction force to the suction pad 76a described above, e.g., orifice 72 in the air passage, to prevent the film 1 from flicked away the suction pad 76a upon release of the suction force.

A film discharge means 17 (FIG. 1) is disposed in the film discharge position of the incubator 12. The film discharge means 17 comprises a suction pad 81 which attracts the film 1 in the cell 42 which has finished with measurement and lifts it, a horseshoe-like delivery member 82 which receives the film 1 from the suction pad 81 and transfers it outside the incubator 12 and a discarding suction pad 83 which receives the film 1 from the delivery member 82 and discards it into a discarding box 84. The suction pad 81 is connected to a suction pump (not shown) through a vacuum tube. The suction pad 81 may also be provided with the mechanism for elongating the time required to release the suction force to the suction pad 76a described above, e.g., orifice 72 in the air passage, to prevent the film 1 from flicked away the suction pad 81 upon release of the suction force.

The sample liquid supplier 14 comprises a turn table 85 which is rotated by a drive mechanism 86. The turn table 85 holds a plurality of sample containers 87 filled with sample liquids which are arranged along the circumferential edge of the turn table 85 and is rotated to bring the sample containers 87 to a sample liquid supplying position one by one. A plurality of nozzle tips 88 which are mounted on a spotting nozzle 91 to be described later are held on the turn table 85 inside the sample containers 87.

The spotting means 15 for spotting the sample liquid onto the film 1 comprises a spotting nozzle 91 which sucks and discharges the sample liquid, and a nozzle tip 88 like a pipette is demountably mounted on the nozzle 91. The nozzle 91 is moved up and down and rotated by a drive mechanism 92. That is, the nozzle 91 sucks the sample liquid from the sample liquid supplier 14, is moved to the film 1 held by the delivery member 73, and then spots the sample liquid onto the film 1. The spotting position is on the path of the delivery member 73 and on or near the intersection of the path of the delivery member 73 and the path of the film take-out member 70. The nozzle tip 88 is changed every time the sample liquid is changed.

The film 1 spotted with the sample liquid is transferred to the incubator 12 and incubated there. After incubation for a predetermined time, the optical density of the reagent layer 3 is measured by the light measuring system 16 (FIG. 1) disposed below the incubator 12. The light measuring system 16 comprises said light measuring head 95 for measuring the optical density of the color formed by the coloring reaction between the reagent layer 1b and the analyte in the sample liquid. The light measuring head 95 projects measuring light containing light of a predetermined wavelength onto the reagent layer 1b through the support sheet 1a and detects reflected light with a photodetector. Light from a light source (lamp) 96 enters the light measuring head 95 through a filter 97 and is caused to impinge upon the reagent layer 1b by the head 95. A plurality of kinds of filters 97 are mounted on a rotary disk 98 which is driven by an electric motor 99 and one of the filters 97 is selected according to the analyte.

The reflected light from the reagent layer 1b carries thereon optical information (more particularly the amount of light) on the amount of coloring substances formed by the coloring reaction between the reagent layer 1b and the sample liquid. The reflected light is received by the photodetector and the optical information carried by the reflected light is converted to an electric signal by the photodetector. The electric signal is input into a determination section through an amplifier (not shown). The determination section determines the optical density of the coloring substances formed by the coloring reaction between the reagent layer 1b and the sample liquid on the basis of the level of the electric signal and determines the concentration or the activity of a predetermined biochemical component in the sample liquid by colorimetry.

The measurement by the biochemical analysis apparatus 10 is effected in the following manner. That is, a cartridge 20 (in the film supplier 11) storing therein chemical analysis films 1 corresponding to the analyte to be analyzed is moved to the film take-out position. In the film take-out position, suction force is applied to the suction pad 70a of the film take-out member 70 and a film 1 is taken out by suction pad 70a. The film 1 held by the suction pad 70a is transferred to the delivery member 73 with the reagent layer 1b facing upward and with the suction force gradually released to prevent the film 1 from being flicked. Then a sample liquid is spotted onto the reagent layer 1b.

That is, a nozzle tip 88 is mounted on the spotting nozzle 91 of the spotting means 15 and the spotting nozzle 91 is moved above a desired sample container 87 in the sample liquid supplier 14. Then the nozzle 91 is moved downward to bring the nozzle tip 88 into the sample liquid and the nozzle 91 sucks a predetermined amount of the sample liquid into the nozzle tip 88. Thereafter the nozzle 91 is moved above the center of the film 1 on the delivery member 73 and moved downward toward the film 1, where a predetermined amount of sample liquid is spotted onto the reagent layer 1b from the nozzle tip 88. The sample liquid spreads over the reagent layer 1b and mixes with the reagent therein.

The film 1 spotted with the sample liquid is inserted into one of the cells 42 of the incubator 12 by the delivery member 73. That is, an empty cell 42 is rotated to the insertion position and the cell cover 64 is lifted together with the film pressing member 61 by the push rod 67. Then the delivery member 73 is inserted into the cell 42. Then the suction member 76 is moved upward to lift the film 1 above the delivery member 73 while holding the film 1 under a suction force. Thereafter the delivery member 73 is retracted and the suction member 76 is moved downward to bring the lower surface of the frameless chemical analysis film 1 in contact with the upper surface of the lower disk 45. Then the push rod 67 is lowered to permit the cell cover 64 to move downward and to cause the film pressing member 61 to press the corners of the film 1 by its protrusions 61b. Then the suction member 76 is moved downward.

Coloring reaction (coloring substance forming reaction) is caused when the film 1 with the sample liquid is heated to a predetermined temperature in the enclosed cell 42 in the incubator 12, and the optical density of the coloring substances is measured by the light measuring head 95 after a predetermined time or at predetermined intervals.

As the means for adjusting the time required to release the suction force to the suction pad 70a may be various known means other than those described above.

What is claimed is:

1. A method of transferring a frameless chemical analysis film having a reagent layer formed on a support sheet comprising the steps of holding the frameless chemical analysis film by a transfer means having a resilient suction pad under a suction force supplied to the suction pad, and transferring the frameless chemical analysis film to a predetermined member by releasing the suction force, wherein the step of transferring comprises gradually releasing the suction force supplied to the suction pad over a period of time taking at least a time which the suction pad, which has been deformed under the suction force, takes to be restored to an original shape.

2. A method as defined in claim 1 in which the time required to release the suction force is elongated by increasing the resistance of an air passage for opening the suction pad to atmosphere.

3. A method as defined in claim 1 in which the time required to release the suction force is elongated by slowly opening an air valve which opens and closes an air passage for opening the suction pad to atmosphere.

4. A transferring device for transferring a frameless chemical analysis film having a reagent layer formed on a support sheet comprising a transferring means provided with a resilient suction cup which holds the frameless chemical analysis film under a suction force supplied thereto through a vacuum line, an air passage which opens the vacuum line to atmosphere and an air flow control means which, when the suction pad is to release the frameless chemical analysis film, controls a flow rate of air in the air passage to gradually introduce air into the vacuum line so that the pressure in the vacuum line increases to a release pressure, at which the suction pad releases the frameless chemical analysis film, taking at least a time which the suction pad, which has been deformed under the suction force, takes to be restored to an original shape.

5. A transferring device according to claim 4, wherein said air flow control means comprises an air valve connecting the suction force and said air passage to the vacuum line.

6. A transferring device according to claim 5, wherein said air flow control means comprises an orifice having a cross-section smaller than said air passage located between said air valve and the atmosphere for controlling the air flow through said air passage to said air valve.

7. A transferring device for transferring a frameless chemical analysis film having a reagent layer formed on a support sheet comprising:

a means for transferring the frameless chemical analysis film;

a means for holding the frameless chemical analysis film to said means for transferring; and a means for gradually releasing the chemical analysis film from said means for transferring wherein the chemical analysis film is gradually released in a manner that results in preventing the reagent layer from being propelled off the support sheet, wherein said means for holding the frameless chemical analysis film includes a suction force which deforms said means for transferring, and wherein said suction force is released by said means for gradually releasing over a predetermined amount of time which is required for said means for transferring to be restored to an original condition.

8. A transferring device according to claim 7 wherein said means for transferring includes a suction cup attached to a vacuum line wherein the suction force of said means for holding is supplied to said suction cup.

* * * * *